(12) United States Patent
Lopez (10) Patent No.: US 7,652,129 B2
(45) Date of Patent: Jan. 26, 2010

(54) PARALLEL PROCESS FOR PROTEIN OR VIRUS SEPARATION FROM A SAMPLE

(75) Inventor: Mary Lopez, Bedford, MA (US)

(73) Assignee: PerkinElmer LAS, Inc., Boston, MA (US)

( * ) Notice: Subject to any disclaimer, the term of this patent is extended or adjusted under 35 U.S.C. 154(b) by 136 days.

(21) Appl. No.: 10/568,215

(22) PCT Filed: Aug. 13, 2004

(86) PCT No.: PCT/US2004/026305

§ 371 (c)(1),
(2), (4) Date: Mar. 28, 2006

(87) PCT Pub. No.: WO2005/025713

PCT Pub. Date: Mar. 24, 2005

(65) Prior Publication Data

US 2007/0020616 A1    Jan. 25, 2007

Related U.S. Application Data

(60) Provisional application No. 60/481,223, filed on Aug. 13, 2003.

(51) Int. Cl.
*A23J 1/00* (2006.01)
(52) U.S. Cl. .................................................... 530/412
(58) Field of Classification Search ........................ None
See application file for complete search history.

(56) References Cited

OTHER PUBLICATIONS

Wagner et al. "An Automated on-line multidimensional HPLC system for protein and peptide mapping with integrated sample preparation", Anal. Chem. 2002 74:809-820.*

Kachman et al. "A 2-D liquid separations/Mass mapping method for interlysate comparison of ovarian cancers", Anal. Chem 2002 74:1779-1791.*

Gygi et al. "Evaluation of two-dimensional gel electrophoresis-based proteome analysis technology", PNAS 2000 97(17):9390-9395.*

Chen, Xian, et al, Site-Specific Mass Tagging with Stable Isotopes in Proteins for Accurate and Efficient Protein Identification, Anal. Chem. 2000, 72, 1134-1143.

Weckwerth, Wolfram, et al, Comparative quantification and identification of phosphoproteins using stable isotope labeling and liquid chromatography/mass spectrometry, Rapid Commun. Mass Spectrom. 14, 1677-1681 (2000).

Kelleher, Neil L., et al, Identification of Modification Sties in Large Biomelecules by Stable Isotope Labeling and Tandem High Resolution Mass Spectrometry, The Journal of Biological Chemistry, vol. 272, No. 51, Issue of Dec. 19, pp. 32215-32220, 1997.

Oda, Y., et al, Accurate quantitation of protein expression and site-specific phosphorylation, Pro. Natl. Acad. Sci. USA, vol. 96, pp. 6591-6596, Jun. 1999.

* cited by examiner

*Primary Examiner*—Karen Cochrane Carlson
*Assistant Examiner*—Bin Shen
(74) *Attorney, Agent, or Firm*—Gifford, Krass, Sprinkle, Anderson & Citkowski, P.C.

(57) ABSTRACT

A sample is divided into a series of aliquots with the aliquots being subjected to at least two successive parallel separation steps in order to resolve protein or viral components thereof. The separation steps are performed not only on a sample but subsamples each containing a prelabeled tag to afford comparisons between subsamples. The parallel separation is amenable to high throughput and automation.

28 Claims, 10 Drawing Sheets

Figure 1

Prior Art

Prior Art

PARALLEL PROCESS FOR PROTEIN OR VIRUS SEPARATION FROM A SAMPLE

RELATED APPLICATION

This application claims priority of U.S. Provisional Patent Application Ser. No. 60/481,223 filed Aug. 13, 2003, which is incorporated herein by reference.

FIELD OF THE INVENTION

The present invention relates in general to separation methods for a protein-containing sample for the purpose of identifying or measuring the sample's constituent proteins, and in particular to the use of stepwise gradients to identify and/or measure a sample constituent protein.

BACKGROUND OF THE INVENTION

In life science research it is often desirable to identify the constituent proteins in a sample. Typically, the sample is extracted from an organism or collection of living cells. Such samples, of which blood serum and cell lysates are representative, are generally composed of many thousands of proteins. In disease or pathway research it is often necessary to assess the protein composition of many such samples in order to correlate the presence, absence or amount of specific proteins to the state of the source organism.

Figure 2:
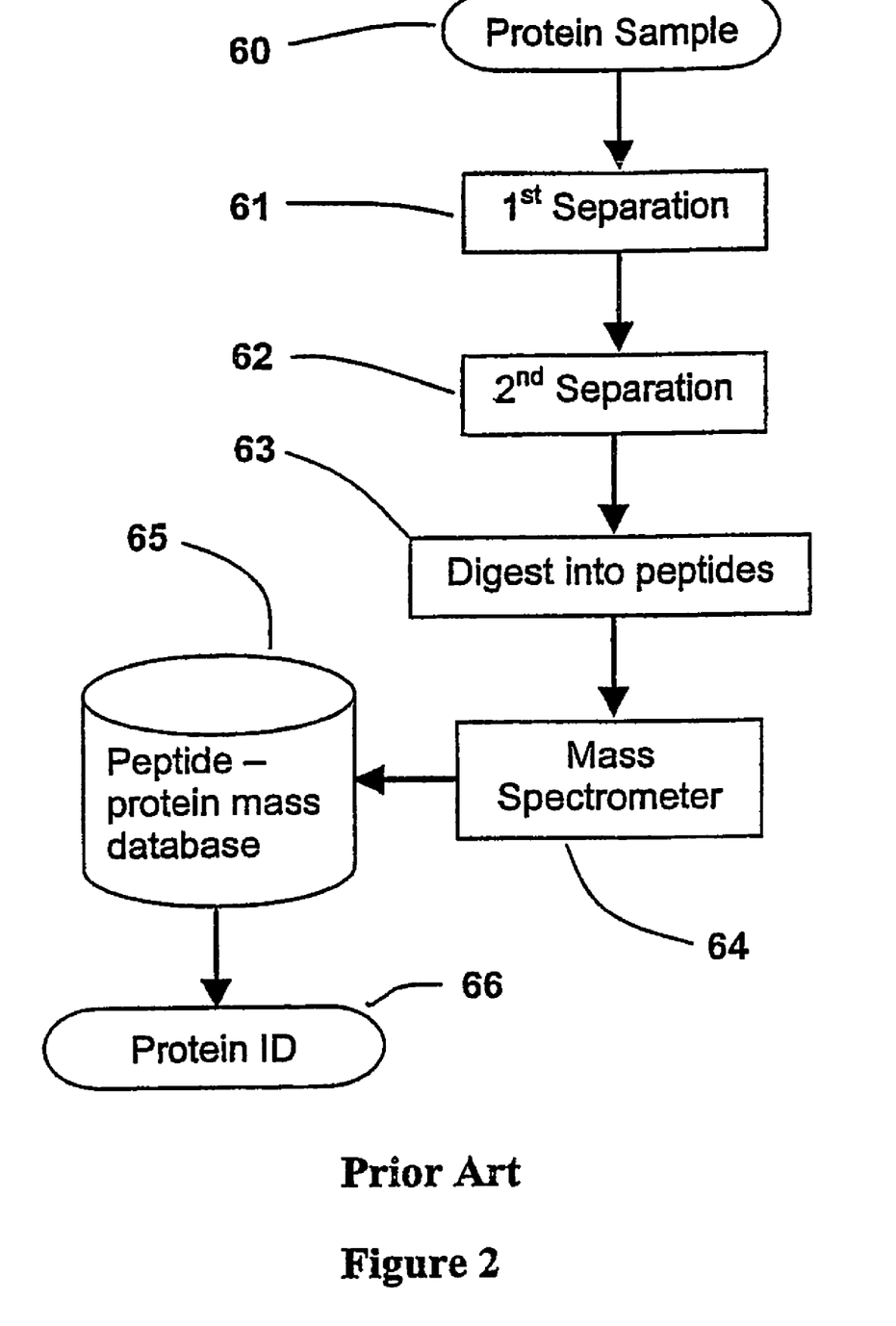
FIG. 2 is a prior art process flow diagram of the general method of protein separation and identification by peptide mass fingerprinting.

Complex mixtures of proteins are typically separated by multiple mechanisms. Common examples of separation parameters are charge, hydrophobic interactions, affinity and molecular weight. After separation into constituent proteins, the identification of constituent proteins is often required. The most common and useful method of protein identification is peptide mass fingerprinting using mass spectrometry. FIG. 2 shows an exemplary prior art process flow diagram. This process uses one, two or more methods (61, 62) for separating constituent proteins in the sample mixture, breaking up the proteins in the sample 60 into peptides with proteolytic digestion 63, most commonly using the trypsin enzyme, and reading the mass spectra of the peptides on a mass spectrometer 64. Depending on the separation mechanisms used, digestion may be performed before either one of the two separations or just before the mass spectrometry measurement. Also, there may be more or fewer separation mechanisms than the two shown in the figure. The resulting mass spectra are compared with peptide spectra from theoretical digests of sequences of known proteins in a database 65 and a plurality of sample protein identifications 66 are produced by correlation of the measured peptide masses to the calculated sequence masses.

Several types of mass spectrometer instruments are used for peptide mass fingerprinting. One type is the Matrix Assisted Laser Desorption Ionization-Time Of Flight (MALDI-TOF). Peptide samples are introduced into MALDI instruments by spotting the liquid solution onto a MALDI target plate, the target plate having been previously coated with a matrix substance that facilitates the ionization of compounds to be measured. The MALDI plate with one or more samples spotted upon one or more of its target areas is then inserted into the spectrometer. A laser beam ionizes the sample spots and ejects the ions into the driving electric fields of the mass spectrometer. An example of a MALDI mass spectrometer is the PerkinElmer prOTOF 2000 orthogonal MALDI which uses 96-, 384- or 1,536-sample MALDI plates with the form factor of flat, thin microplates.

Another type of mass spectrometer instrument used for peptide mass fingerprinting is the electro-spray ionization mass spectrometer (ESI). Sample introduction of ESI instruments may be a continuous or near-continuous flow of liquid unlike the batch loading of discrete samples required by the MALDI. In this continuous flow case, measurements are taken serially at periodic time intervals against a continuous inflow of peptides to be characterized.

Separation of the protein mixture may be performed in a variety of separation matrices. A separation matrix is a support that has size, porosity and functionality characteristics in order to enable interaction with, and separation of, molecules. Typical supports for separation matrices include silica, alumina, agarose, acrylamide, styrene divinylbenzene, glass, dextran, polystyrene, acrylics, nylon, polyvinylidene difluoride, and combinations thereof. The separation matrix support can be in a form typically found for chromatography resins such as particles, gels, membranes or any other form that enables suitable separation characteristics. A flow-through vessel that holds a separation matrix is commonly called a column.

The functionality characteristics of the separation matrix support enable interactions with molecules. These functionalities can be cationic or anionic to allow for charge based interactions; alkyl chain, usually in the three to eighteen carbon length to allow hydrophobic interactions; or affinity ligands for specific binding interactions. The support may also have porosity characteristics that cause a molecular weight based separation as the molecules flow through it.

Figure 3:
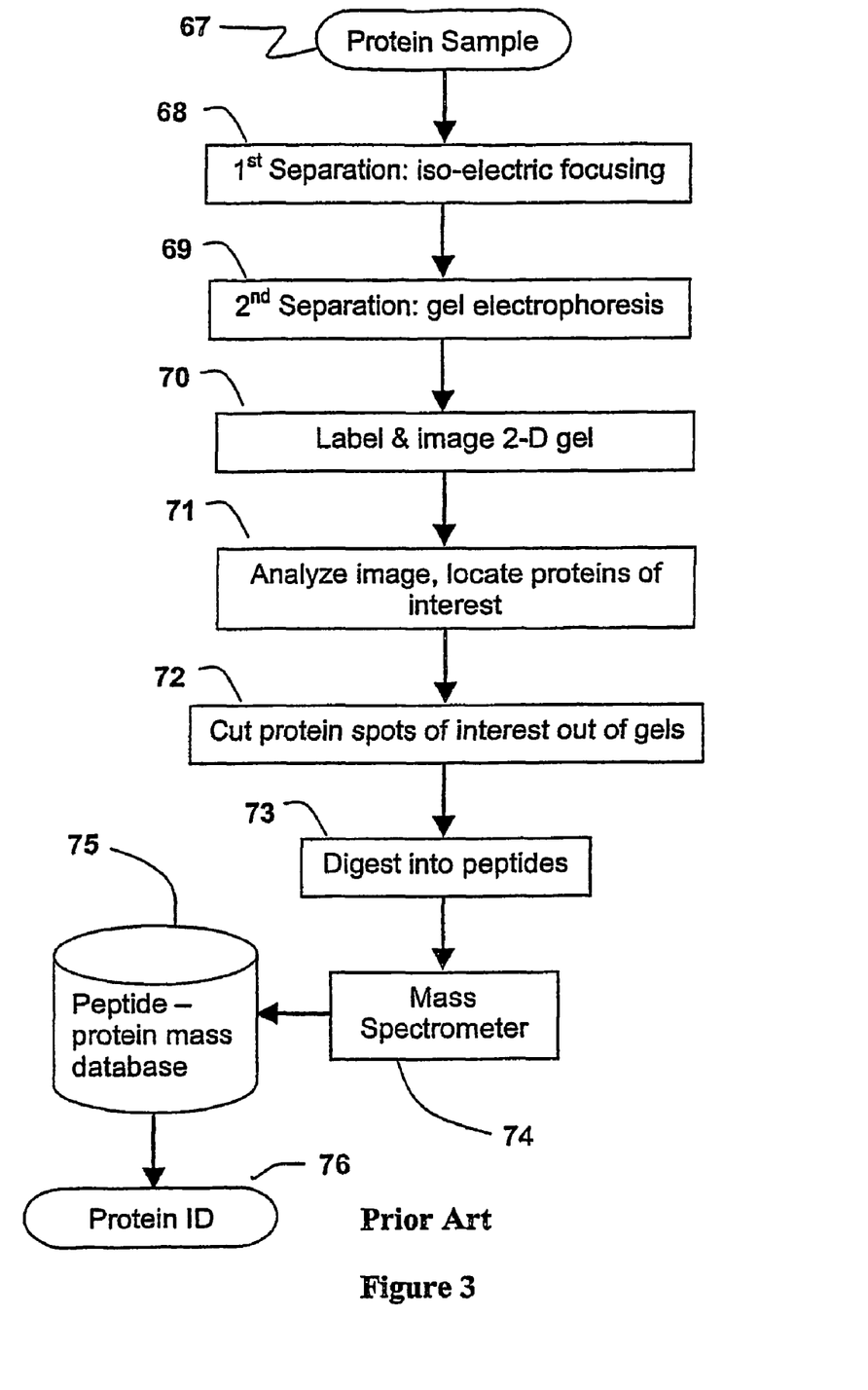
FIG. 3 is a prior art process flow diagram of the prior art method of separating and identifying proteins using two-dimensional gel electrophoresis followed by peptide mass fingerprinting.

The most established analytical method of separating and identifying proteins is two-dimensional gel electrophoresis (2-D gel) followed by MALDI mass spectrometry. The major steps of this process are shown in the flow diagram of prior art FIG. 3. The complex sample mixture 67 is first separated by charge (pH) by an electrophoresis process called isoelectric focusing 68. This produces a linear strip of gel material with the proteins separated by charge along the length of the strip. The strip is placed in contact with the edge of a two-dimensional polyacrylamide gel sheet in the appropriate buffer and voltage is applied to separate the proteins according to molecular weight via gel electrophoresis 69. Individual proteins form spots of varying sizes and shapes across the gel. The proteins are labeled 70 either before or after separation, typically either through staining or fluorescent labeling. The labeled 2-D gel is imaged and the image is analyzed 71 to identify specific spots representing the location of specific proteins in the gel. The spots of proteins of interest are cut out of the gel 72 and digested to peptides 73, typically with trypsin. The peptide solution is then typically spotted onto a MALDI plate to facilitate peptide mass fingerprinting using a mass spectrometer 74 and a mass database 75 to produce protein identifications 76.

A common extension to the 2-D gel process is assessment of differential protein expression between two complex samples, samples from normal and diseased organisms for example. One typical process for differential separation on 2-D gels is to label all of the proteins in each sample with a different fluorescent dye (Patton et al. Current Opinion in Biotechnology 2001 6:63-69). The samples are then mixed, the 2-D gel separation is performed, and then the imaging is performed separately at the wavelengths of each of the two fluorescent dyes. In theory, proteins that exist in common in both samples will produce 2-D gel spots that are coincident. Proteins that exist in one sample but not in the other will produce spots at only one of the wavelengths. Further, proteins that exist in both samples but in different concentrations can be assessed by the ratio of their fluorescent intensities at the two wavelengths. Another typical process for differential measurements on 2-D gels is digital correlation of protein spots in images from two independent gels, and quantitating the differences in protein amount in each gel. This method suffers from its dependence on multiple 2-D gels producing protein spots in a reproducible manner.

Among the shortcomings of the 2-D gel process are the degree of skill required to perform the process, the large amount of manual manipulation of reagents and gels required, the lack of repeatability and reproducibility of results, and the length of time required for the process, which is often two or three days. Also, the assessment of differential protein expression using two dyes is limited by the dyes' ability to label all proteins to produce fluorescent signals proportional to their concentrations and by the fluorescent dyes' effects on the separation process, as well as limits to spot finding and quantitation at the image processing step. In an attempt to address these shortcomings another approach to the task called MUlti-Dimensional Protein Identification Technology (MUDpit) has been developed as depicted in prior art FIG. 4.

The MUDpit process utilizes liquid chromatography (LC) rather than gel electrophoresis as the separation modality. Referring to prior art FIG. 4, a protein sample 80 is first digested to peptides 81, then LC drives the peptide sample mixture through a flow-through column 84 containing a separation matrix while varying the concentration of the separation buffer, typically with a constant fluid flow rate and a linear concentration gradient with time. The buffer concentration gradient is typically produced by linearly varying the flow rates of two buffer solutions 82 and 83, one flow rate increasing while the other decreases, keeping the total flow rate through the LC column constant.

Figure 4:
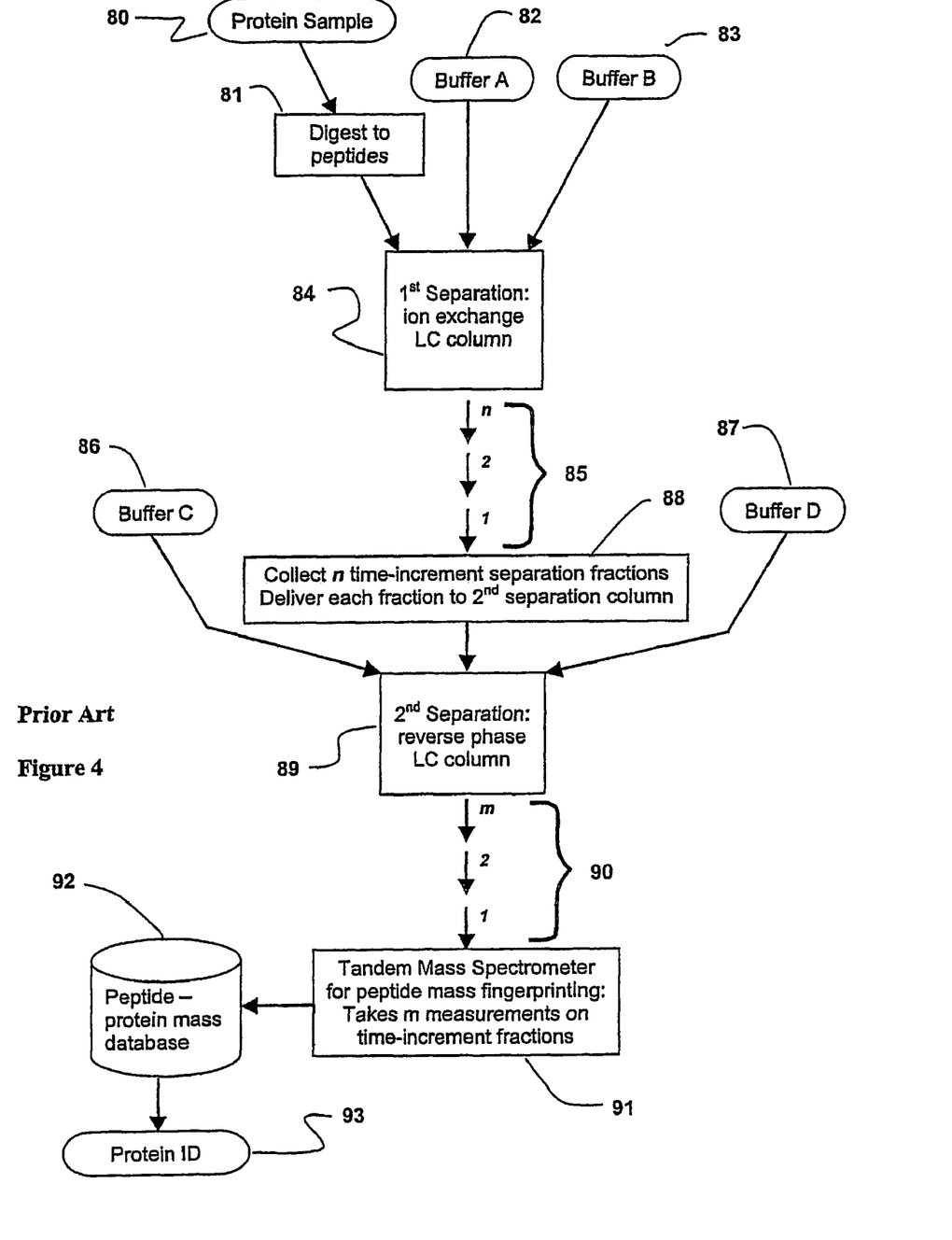
FIG. 4 is a prior art process flow diagram of the prior art method of separating and identifying proteins using two-dimensional liquid chromatography followed by peptide mass fingerprinting.

Unlike 2-D gels which produce separations as physical spots with specific locations on a 2-D plane, LC produces a series of volumes of eluted solutions (fractions) that are typically sampled at uniform time increments from a flowing output stream at the output port of a column 85. The LC process is inherently serial in nature; the fractions are delivered out of a single column one after the other. The MUDpit process further utilizes two complete LC processes in series to produce two dimensions of separation analogous to the 2-D gel process. The first separation is generally performed on an ion-exchange column and the second on a reverse-phase column. Time increment fractions are collected from the output stream of the first column 88, then each of those fractions is run independently on the second separation column 89 to generate a second series of time-increment fractions 90. Often the output of the second column is directed continuously to the input of a mass spectrometer, typically an electrospray tandem mass spectrometer 91. In this arrangement the continuous flow from the second column is directed to the mass spectrometer instrument and the time-increment fractions are generated by the mass spectrometer's sampling of the stream. Other variations of MUDpit utilize multi-modality columns, capillaries and other variations of detailed configuration but retain the significant operational details described here.

The MUDpit process can be adapted to differential analysis between two samples by labeling the proteins or peptides with mass tags prior to separation (Patton et al., Current Opinion in Biotechnology 2002 13:321-328). Mass tags are molecules of known, small molecular weight that can be resolved by the mass spectrometer but do not materially affect the separation process. Mass spectra of identical peptides from two mass tag-labeled samples will have the same form but will be shifted along the mass axis by the difference of the mass of the tags, so their spectra can be differentiated. The ratio of the paired spectra's signal levels are representative of the relative concentrations of the protein in the two samples.

The use of mass tags for differential protein analysis has been described extensively in the literature. Mass tags can be isotopes of the constituent atoms of the proteins, such as $N^{15}$, $C^{14}$ or $H^2$ or can be larger such as a $CH_3$ group replacing a hydrogen atom. Labeling proteins with mass tags can be performed biologically in cell culture by using a culture media containing isotopic compounds as has been described by Oda et al., PNAS Jun. 8, 1999; 96(12):6591-6596 and Chen et al., Anal. Chem. Feb. 16, 2000; 72, 1134-1143, for example. Mass tags can also be applied directly to proteins by chemical labeling as described by Weckwerth et al. (Rapid Commun, in Mass Spectrom. 14, 1677-1681; 2000) and Kelleher et al. (Journal of Biological Chemistry, Vol. 72, Dec. 19 1997, 32215-32220).

An advantage of the MUDpit process over the 2-D gel process is the degree of automation that can be applied. The LC process is typically hands free. The output of the final LC column can be plumbed into an electro-spray mass spectrometer to deliver the samples to the measurement instrument automatically.

The MUDpit technique also has disadvantages. First, the proteins must be digested to peptides before any separation is performed. This limits the resolution and range of separations as it makes the peptide mixture for the first separation an extremely complex one with potentially millions of different peptides to be discriminated. Short peptides may even overlap between multiple proteins. Second, the dynamic range of the LC process on peptides is lower than that of 2-D gels on intact proteins, so the signals from peptides from high-abundance proteins are more likely to overwhelm signals from low-abundance proteins. These problems are more pronounced when using MUDpit for differential measurements on low-abundance proteins. Further, since the separation elements in MUDpit are inherently serial rather than parallel, the throughput of the process is limited, making the elapsed time to evaluate a sample long even though the process can be largely automated.

Thus, there exists a need for an automated method, system, apparatus and kit for separation and identification of proteins that are more reproducible than 2-D gels. Additionally, the ability to avoid protein digestion prior to the first separation process and allow separations to be done in parallel would also prove beneficial. Such a method and system that supports differential protein analysis when needed would also prove beneficial.

SUMMARY OF THE INVENTION

A process for separating proteins or viruses within a sample includes dividing a sample containing proteinaceous or viral components into multiple aliquots. The multiple aliquots are applied in parallel to a first separation step to yield partially resolved eluates. The partially resolved eluates are then subjected in parallel to a second separation step. Subsequent to the first separation step, digestion of the partially resolved eluates is optionally performed. Analysis of fractions derived from the second separation step containing digested fractions in combination with analysis of undigested material corresponding to the same aliquot often facilitates characterization. Prior to separation, a subsample is optionally labeled with a unique tag and combined with another subsample to yield the separation sample. Tag analysis provides information about the relative quantity of a particular constituent between subsamples after separation according to the process detailed herein.

A kit is provided that includes two separate separation steps and instructions for the parallel separation of a proteinaceous or viral component containing sample through the use of separation buffers. A kit and process as detailed herein are particularly well suited to provide samples for subsequent mass spectrometry analysis to generate a characterization library for constituent components.

Additional efficiencies are achieved through the use of a system for proteinaceous or viral component containing sample separation that includes a pipetting robot, a first separation matrix, and a second separation matrix, the first separation matrix and second separation matrix maintaining well addresses therebetween for optimal efficiency. Labeling the first separation matrix and second separation matrix with a machine-readable label combined with a machine reader and gripper robot coupled to the pipetting robot further enhances automation and efficiency of the system.

DETAILED DESCRIPTION OF THE INVENTION

The present invention has utility as a method for parallel automated protein or virus separation and identification. The ability to detect and optionally purify proteins or viral populations from a given sample in a parallel manner according to the present invention affords efficiency and speed compared to conventional sequential techniques. The parallel analysis of the present invention is amenable to rapid field detection of proteinaceous or viral pathogens associated with disease outbreaks, bioweapon screening, and the like. A sample is divided into a series of aliquots with the aliquots being subjected to at least two successive parallel separation steps in order to resolve protein components or viral components therefrom. A digestion after the first separation or second separation often facilitates subsequent analysis.

While the present invention is detailed hereafter with respect to protein analysis, it is appreciated that the present invention is likewise well suited to analyze a sample containing multiple viral genera, multiple viral species, or multiple viral strains. Such a viral analysis is of value in evaluating the therapeutic effects of an antiviral treatment on the incident viral population.

Protein or virus concentrations are readily discerned following separation steps as detailed by resort to a conventional correlative analysis technique such as mass spectrometry, fluorescence labeling tags, radioactive labeling tags, and binding assays. Differential concentrations are obtained for multiple samples through the use of correlative mass tags, tags as detailed above, or binding assays. Subsamples each having a unique tag are readily mixed to form a sample. Label analysis provides comparative data between subsamples.

Figure 1:
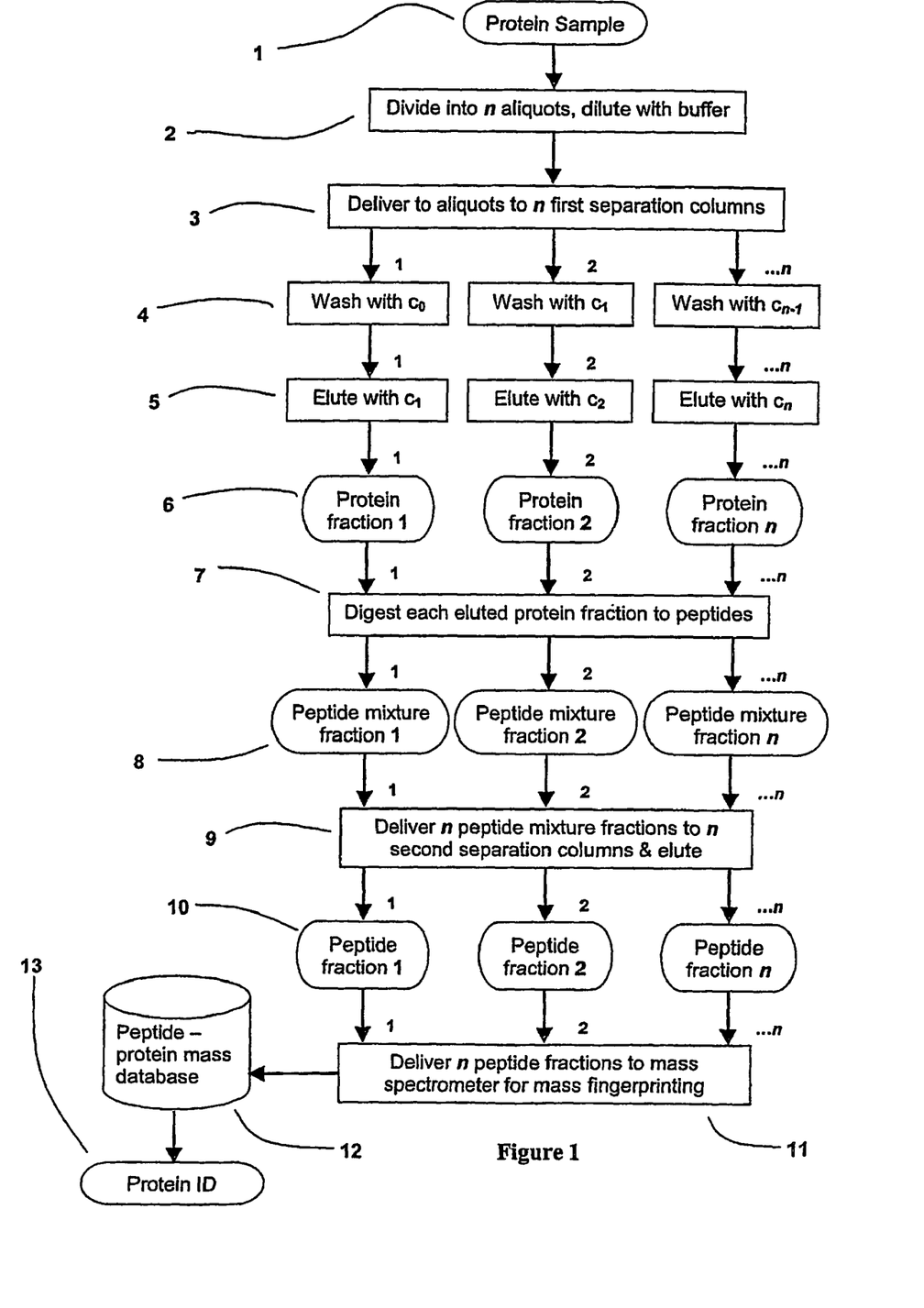
FIG. 1 is a process flow diagram according to the present invention for parallel separation.

One aspect of the present invention is the use of multiple separation columns in parallel. A general process flow diagram is shown in FIG. 1, where the starting protein sample mixture 1 is divided into n approximately equal aliquots diluted with a buffer 2. The number of aliquots, n, is both the degree of parallelism in the subsequent separation step and the number of fractions into which the sample is separated in a first separation step. These sample aliquots are next delivered to each of n first separation columns 3. The first separation step provides at least partial resolution of proteins or viruses within a sample aliquot of the parallel separation process based on separation techniques illustratively including separation based on charge, molecular weight, and hydrophobicity. In the preferred embodiment, the first separation step is an ion-exchange separation. The Vivascience® plate represents a commercially available matrix well plate suitable for ion-exchange separation. A first set of separation buffers, the members of the set numbering n+1, are used for the first separation step. The buffers in this set are formulated in any number of ways including variation in components, concentration, pH, ionic strength and the like. Preferably, the buffer set varies monotonically with increasing or decreasing steps of concentration $c_0, c_1, c_2 \ldots c_n$ (hereinafter referred to as a stepwise gradient) corresponding to the desired range of first separation conditions.

In the instance of ion-exchange, the parallel sample aliquots are then washed with the set of first step gradient separation buffers as shown at 4 in FIG. 1, where sample aliquot 1 is washed by $c_0$, sample aliquot 2 is washed by $c_1$, and so on through the n samples. After washing, the sample aliquots are all eluted in parallel with a set of buffers 5. Preferably in the instance of ion-exchange separation, the buffer used for elution is a concentration variant. More preferably, the elution buffer is shifted by an increment of concentration. With separation techniques such as size exclusion, elution occurs with the separation buffer until the sample proteins or viruses travel beyond the separation media. In this illustrative example, sample 1 is eluted with $c_1$, sample 2 with $c_2$, and so on. Each sample fraction in this illustrative embodiment has unique but separate conditions where the conditions are adjacent in concentration space in a most preferred embodiment.

The outputs of this first separation process 6 are n partially resolved eluate solution fractions. In the instance of first separation being by ion-exchange, the separation is by charge (pH) if the first set of separation buffers utilized a stepwise gradient of pH or separated by ionic strength if the first set of separation buffers utilized a stepwise gradient of salt concentration. These partially resolved eluate fractions 6 are composed of intact proteins or viruses separated by one parameter.

With further reference to FIG. 1, the protein fractions are digested to peptides in parallel 7 prior to a second separation step. A variety of protein digestion techniques conventional to the art are operative herein illustratively including enzymatic digestion such as with trypsin, chymotrypsin, pepsin, or elastase; photolysis; acid hydrolysis; and thermolysis. While the resolved fractions 10 exiting the columns 9 are readily used as production purified proteins or viruses, it is appreciated that when the sample contains or may contain unknown species that subsequent analysis occurs. In FIG. 1, there are n peptide fractions 8 that are then delivered to n parallel second separation columns 9. The second separation step 9 is appreciated to include any of the separation techniques of charge, molecular weight and hydrophobicity with the recognition that duplicate separation techniques between the first and the second separation steps is generally an unproductive redundancy. The second separation step 9 is also appreciated to be a purification process such as desalting, or concentrating; or a further fractionation process. In FIG. 1, the second separation step is depicted as a fractionation process. The output resolved fractions 10 are then delivered to a mass spectrometer 111 for peptide mass fingerprinting 12.

Figure 5:
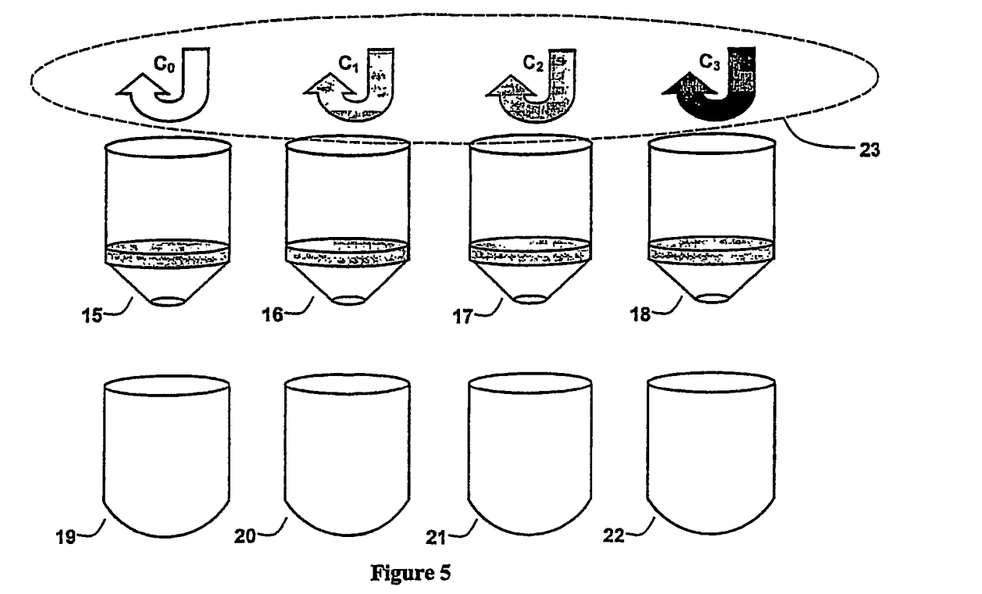
FIG. 5 is a schematic of four separation columns being washed by buffers of four different concentrations, $c_0$ to $c_3$.
Figure 6:
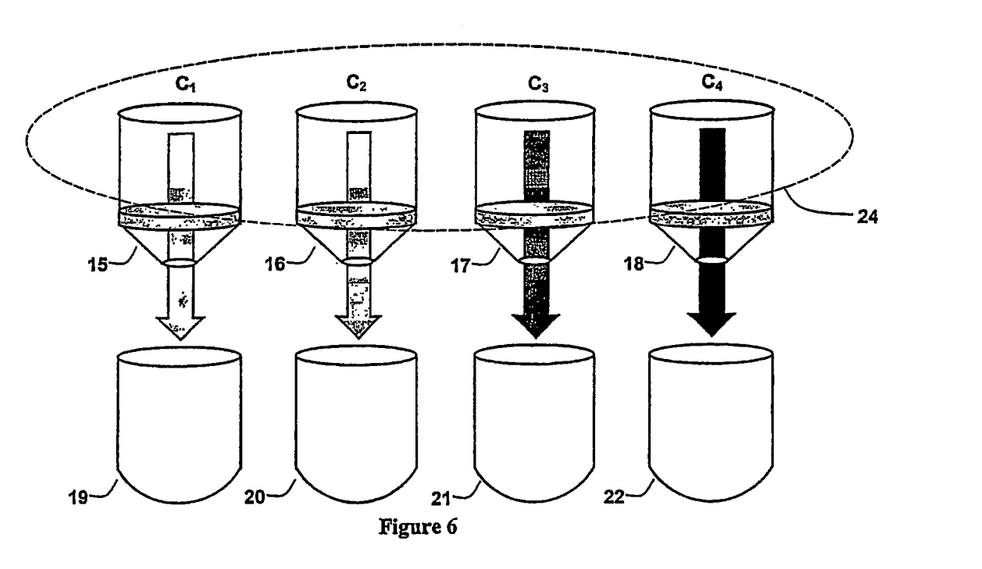
FIG. 6 is a schematic of the four separation columns of FIG. 5 being eluted into four collection vessels by four concentrations of the same buffer, $c_1$ to $c_4$.

FIGS. 5 and 6 show in greater detail washing for the preferred ion-exchange first separation step 4, FIG. 1, and eluting of step 5, FIG. 1, in a first separation process where n=4. There are four separation columns 15, 16, 17 and 18 along with four corresponding collection vessels 19, 20, 21 and 22. A subset of first separation buffers 23 with concentrations $c_0$ through $c_3$ are shown washing the separation columns in FIG. 5. In FIG. 6 an incremented subset of separation buffers 24 with concentrations $c_1$ through $c_4$ is shown eluting through the separation columns, delivering the separated fractions as eluents into the collection vessels 19 through 22.

In the preferred embodiment multiple separation matrices are packaged into a microplate format, such as the Vivascience Vivawell® 96 IEX ion-exchange separation plate kit (Vivascience AG, Hannover, Germany) or the Millipore Multiscreen Separation System reverse-phase separation plate kits (Millipore Corporation, Bedford Mass.). It is appreciated that higher density microplates such as 384-well and higher are operative herein and as beneficial for performing complex or high resolution. Conventional plates are typically provided in a two-plate set including a separation plate containing the separation matrix and a passive collection plate.

It is appreciated the number of wells in the separation plate and the number of parallel separations, n, are independent of one another. While, for instance, a 96-well format makes it convenient to perform separations where n=96, if sufficient separation resolution is obtained with n of 48, 32, 24, 16, 12 or less, the parallelism of the present invention is still advantageous. With smaller values of n, a larger number of samples can be separated with one plate. On the other hand, if an application requires such resolution that n=96 is not sufficient, a sample is readily divided into aliquots over multiple plates to achieve the desired resolution the separation technique can support.

Figure 7:
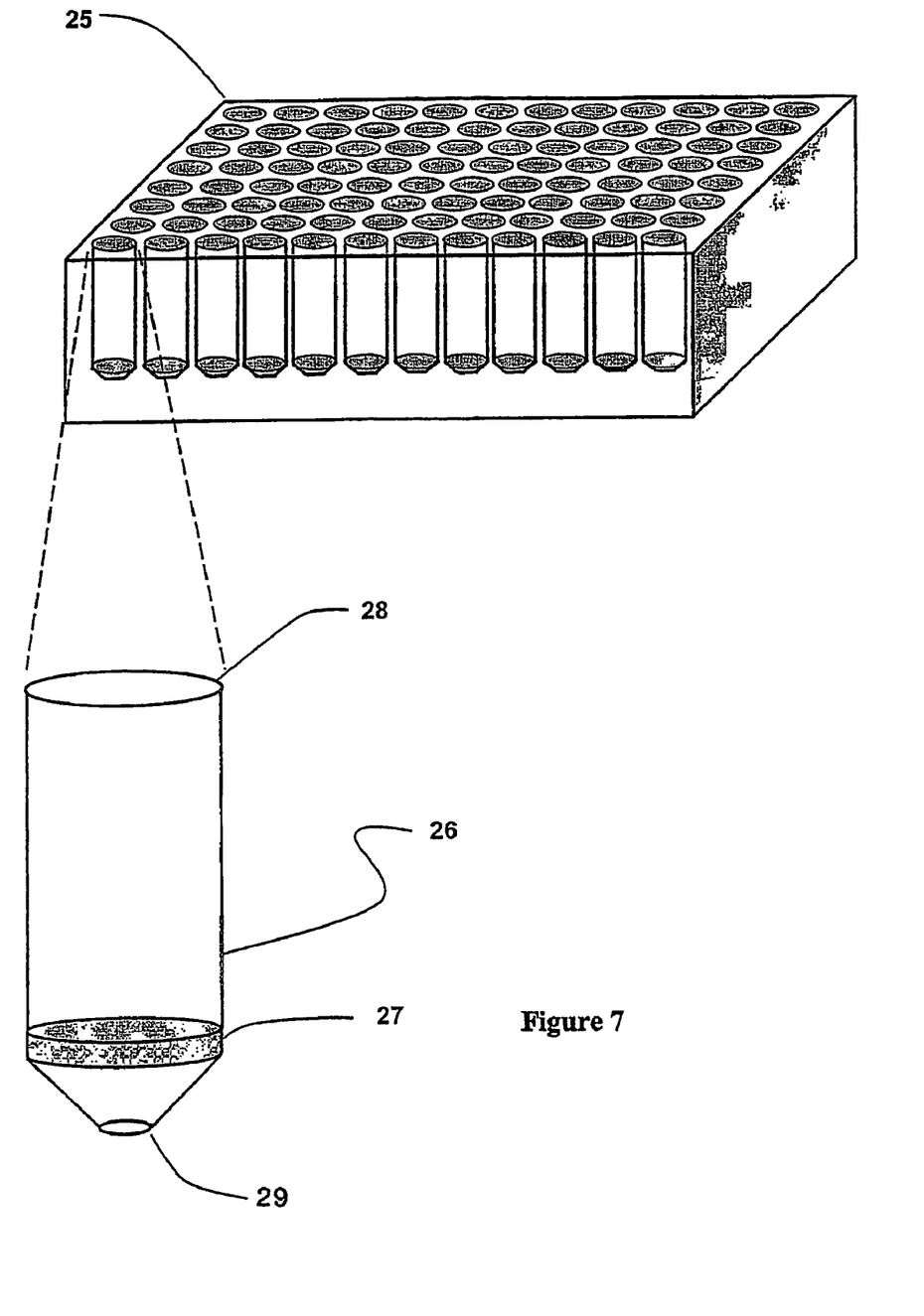
FIG. 7 is a perspective view of a two-dimensional array of separation columns in the form of a deep-well 96-well microplate, depicting as an inset a well forming an open-ended vessel with the separation matrix mounted within.

FIG. 7 shows a separation plate generally at 25 with a detailed view of a well thereof 26. A separation matrix 27 is mounted in the well 26 such that the input aliquot or partially resolved eluate, with or without buffer, can be placed on top of the separation matrix through the open well top 28. Eluents that pass through the separation matrix 27 flow out of the bottom of the well through outlet port 29. The eluents can be collected from the port 29. Optionally, centrifugal force, vacuum or pressure is applied to induce eluent flow through the matrix 27. Preferably, vacuum is applied to the outlet port 29 to draw an eluent through the matrix 27.

Figure 8:
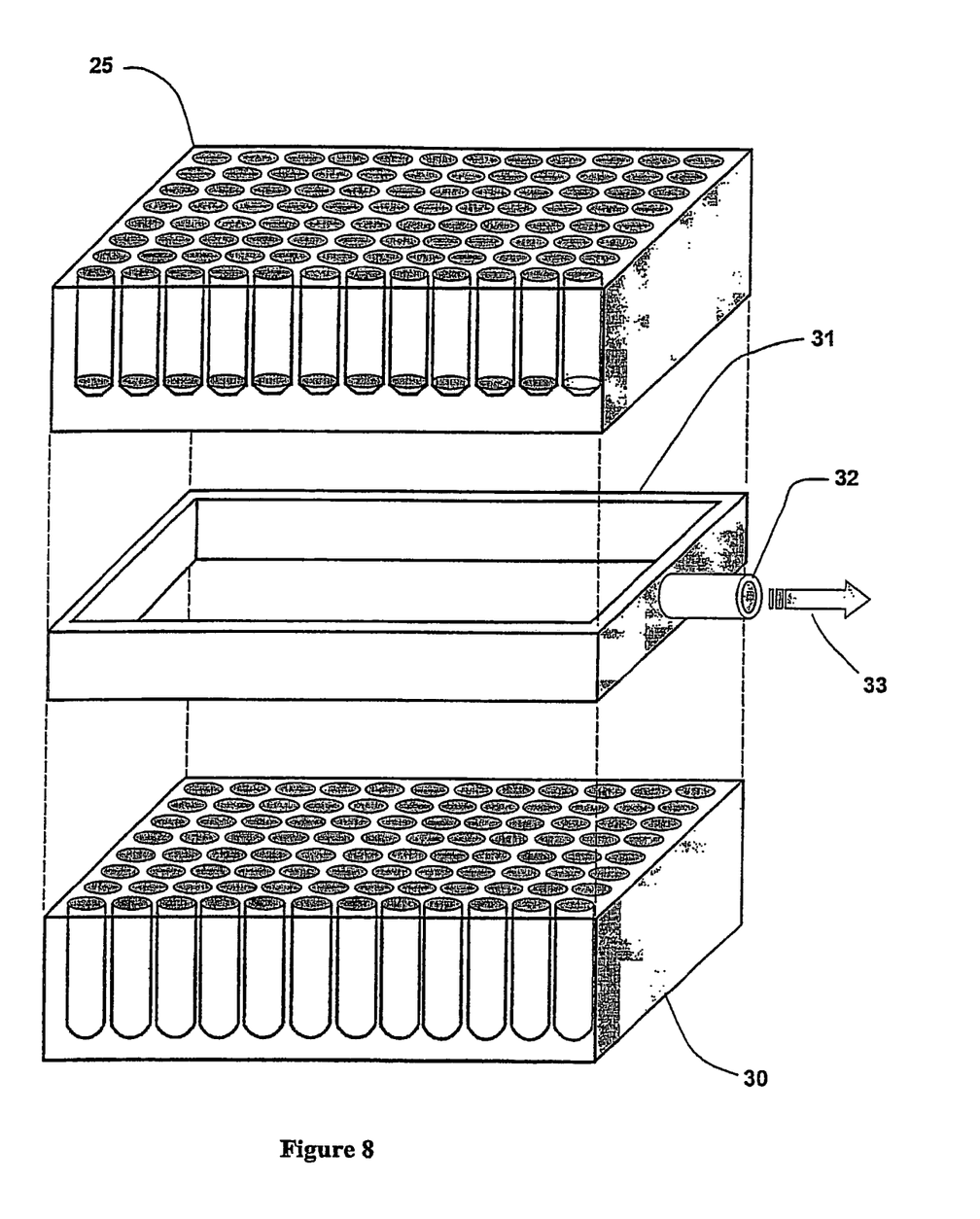
FIG. 8 is an exploded view of the 96-well microplate separation column assembly of FIG. 7 configured with a vacuum manifold and a deep-well plate oriented to draw eluent through the separation columns and into the wells of the collection plate.

FIG. 8 shows the separation plate 25 and a collection plate 30 with a vacuum manifold 31 interposed therebetween. The two plates 25 and 30 and the manifold 31 are assembled in an effectively airtight stack in the order shown and a vacuum of from 0.01 to 50 torr is drawn on vacuum port 32. This vacuum draws eluent out of each of the wells in the separation plate 25, and allows the eluent to pass unimpeded through the vacuum manifold 31 to be deposited in the corresponding well of the collection plate 30. It is also appreciated that this configuration is operative with a first, second or subsequent separation step.

The use of separation plates, such as filter plates, along with vacuum manifolds and collection plates is well established in automated processes such as DNA purification. The use of components with outline dimensions approximating those of SBA standard microplates facilitates automation with a variety of optional robots. In the preferred embodiment, the pipetting robot is a PerkinElmer MultiProbe II™ with the Gripper Integration Platform (PerkinElmer LAS, Boston, Mass.). The robot, when present, executes a predefined sequence of actions defined as a protocol under computer control. The robot grips, lifts, relocates, lowers, and releases inventive separation step such as a microplate as well as pipetting liquid samples. Using such a robot the stacking of collection plate, manifold, and separation plate are automatically assembled and disassembled, allowing the pipetting robot access to the wells in either plate whenever needed by the preselected protocol.

The process of FIG. 1 is performed in an automatic hands-free manner by a general-purpose pipetting robot equipped with a gripper actuator and programmed and equipped with appropriate labware. The preparation of the sets of step-gradient buffers can be done before the analysis process begins, or each member of the set can be formulated and mixed in the separation well by pipetting appropriate volumes of the two constituents. The sample to be separated is first diluted to the desired concentration with the appropriate buffer, then divided into n aliquots and delivered to the first separation step wells. The set of first stepwise-gradient separation buffers are then pipetted into the wells. Vacuum is drawn on the first separation wells to deliver n first separated protein mixtures in parallel to the wells in the collection plate. Next, the stack of separation plate and vacuum manifold are disassembled by the gripper, exposing the collection plate with the separated intact protein fractions.

The pipetting robot is optionally fitted with one or more barcode readers. Individual microplates and other reagent vessels and consumables carry labels with unique identifiers encoded into barcodes. The barcodes are read either by passing the consumable item past a stationary reader using the gripper or by a moving barcode reader attached to the robot's moving head. The barcode reader is interfaced to the pipetting robot's control computer. As a single protein analysis project may utilize dozens of identical-looking plates and other consumables, the robust correlation of sample identification to the resulting data is enhanced by automation. Other types of machine-readable identifiers, such as RF ID tags, are appreciated to fulfill the same function.

After the first separation step 4, trypsin and the appropriate buffers are added to the wells of the collection plate and allowed to incubate to digest the proteins 7. The collection plate containing the peptide mixtures 8 is then moved to another position on the robot deck by the gripper, and a new stack of second collection plate, vacuum manifold, and second separation plate is assembled 9. The peptide mixtures 8 from the first collection plate are pipetted into the second separation plate 9, maintaining the same well addresses in each of the two plates. The peptide mixtures 8 are then followed into the wells of the second separation plate by the set of stepwise gradient second separation buffers. A vacuum is then applied to the vacuum manifold drawing the peptide mixtures 8 in parallel through the second separation plate 9 into the second collection plate. The stack is once again disassembled to expose the second collection plate. The separated peptides 10 can then be pipetted from the plate onto a MALDI target 11.

Figure 9:
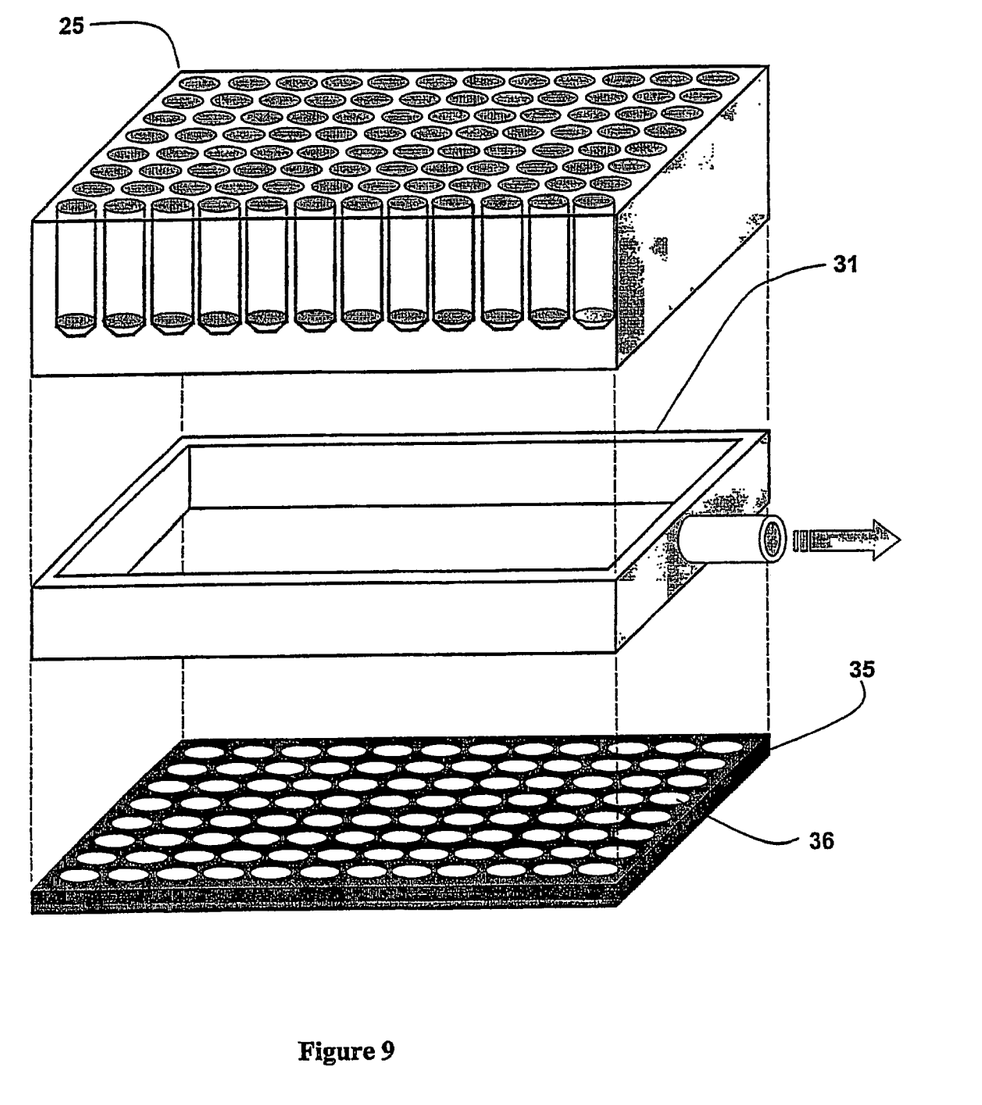
FIG. 9 is an exploded view of the 96-well microplate separation column assembly of FIG. 7 configured with a vacuum manifold and a 96-target MALDI plate oriented to draw eluent through the separation columns and directly onto the target spots of the MALDI plate.

FIG. 9 shows an alternate configuration of a separation plate 25 and vacuum manifold 31 that may be used with a second or final separation step. In this configuration the vacuum draws eluent from the sample plate directly onto MALDI targets 26 on a MALDI plate 35. This avoids an additional pipetting step that would be required if the eluent is collected into a second collection plate and then pipetted onto the MALDI targets. The MALDI plate in the preferred embodiment is a PerkinElmer 96-target MALDIchip™ (part number N701 0040), although it is appreciated that a variety of MALDI plates are operative herein. The MALDIchip™ has SBS-standard outline dimensions and is readily manipulated by plate-gripping robot actuators.

Figure 10:
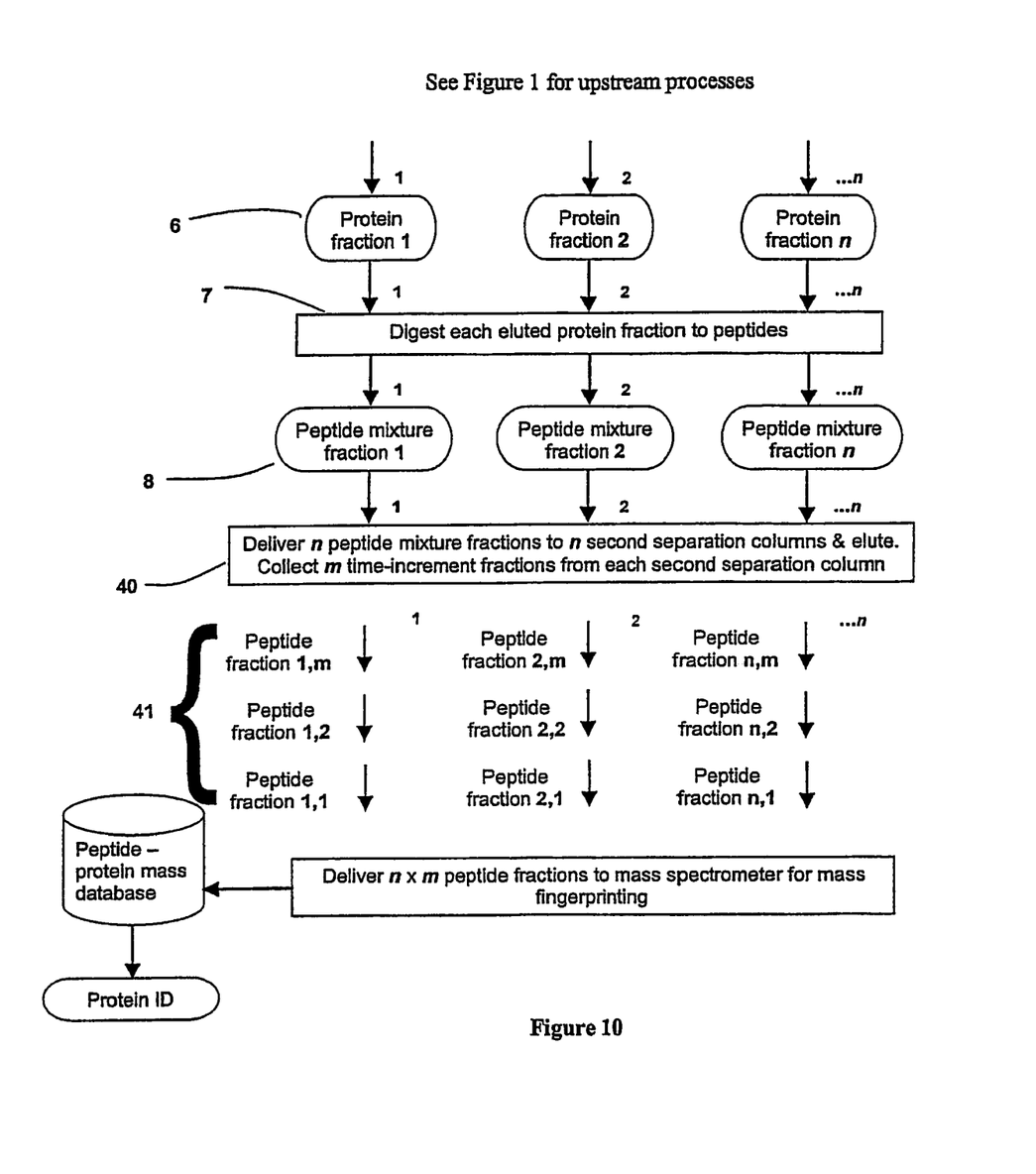
FIG. 10 is a partial process flow diagram of an embodiment of the parallel separation method of the present invention where multiple time-increment fractions of eluent are taken from the second separation columns.

FIG. 10 shows a process flow diagram according to the present invention with an additional dimension of protein separation step. The steps 1-8 are precedent to the additional temporal separation steps depicted in FIG. 10. Like numerals used in FIG. 10 have the same meaning as those detailed with respect to FIG. 1. After first separation and digestion, n peptide mixture fractions 8 are delivered to n second separation columns 40. In this case, m time-increment fractions 41 are eluted from each of the second separation columns and collected separately. In the preferred embodiment, m is in the range of approximately 2 to 25 and most preferably in the range of 2 to 5. The fractions are drawn in parallel from multiple plate wells, but serially in time. In an exemplary case of reverse-phase second separation columns with m=3, three different collection plates or three different MALDI plates are each eluted upon one after another, each receiving a different fraction with different hydrophobicity. This additional separation step adds a true second dimension to the automated protein separation process while retaining the high degree of parallelism and automation.

Figure 11:
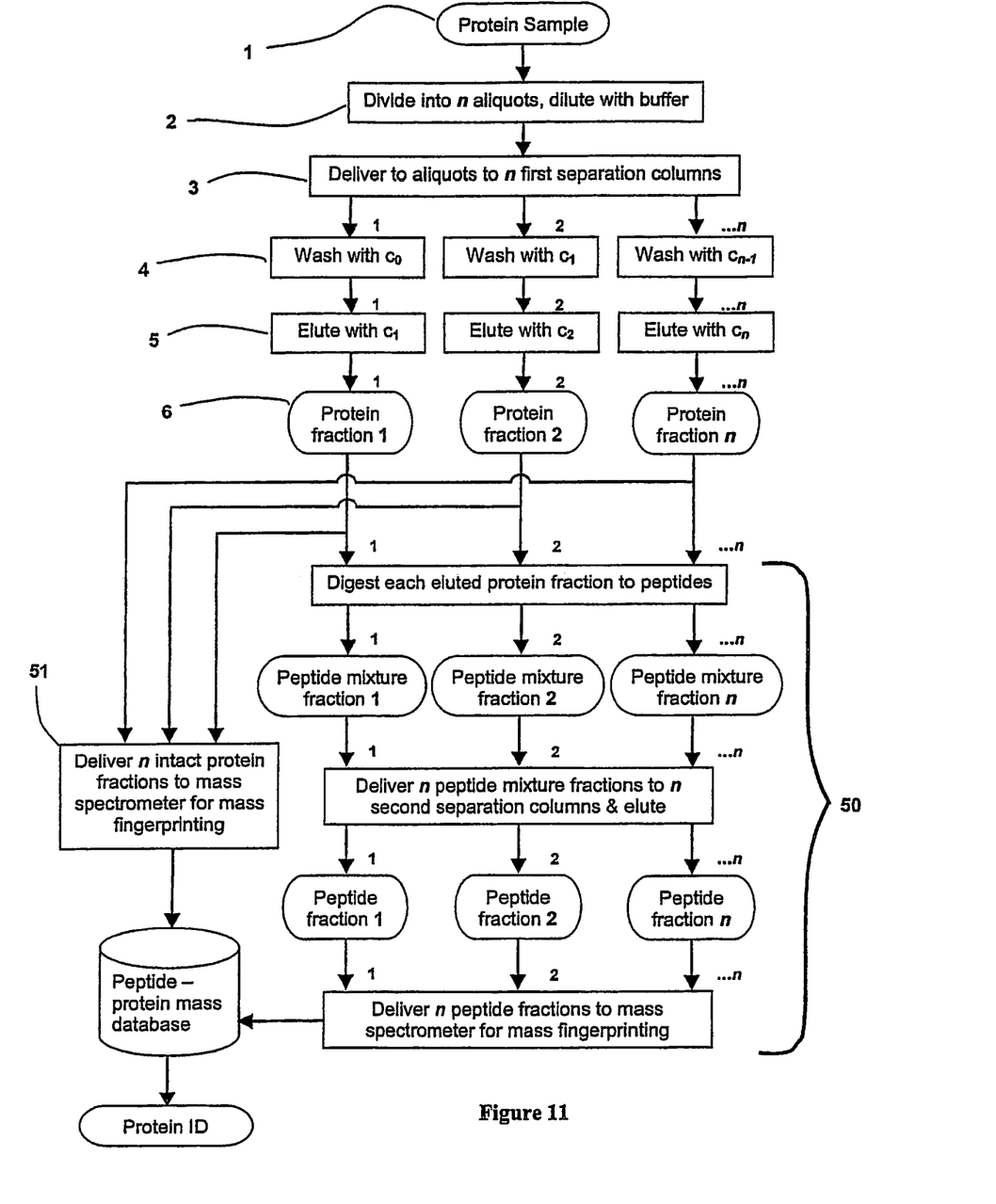
FIG. 11 is a process flow diagram of an embodiment of the parallel separation method of the present invention where mass spectra of the intact proteins eluted from the first separation columns are measured with mass spectrometer in addition to constituent peptides of the proteins.

FIG. 11 shows a process flow diagram according to the present invention where intact proteins as well as digested fragments thereof are both delivered for analysis. The steps 1-6 are the same as those detailed with respect to FIG. 1, to yield n fractions of intact proteins 6. The subsequent processes of digestion and second separation are depicted collectively at 50. The digestion and secondary separation steps are those detailed herein. The fact that intact proteins have been separated prior to digestion to peptides has value in narrowing a database search. Fractions of the partially resolved eluates 6 are shunted for analysis such as measurement by a mass spectrometer 51. Measuring the mass of the intact proteins in addition to the peptide fragments derived therefrom provides an additional constraint on the database search, which in turn produces a higher success rate of valid protein identifications from the peptide mass measurements.

A suitable mass spectrometer is an orthogonal MALDI-TOF such as the PerkinElmer prOTOF 2000™. The orthogonal instrument geometry decouples the ionization ejection velocity from the electric-field induced time-of-flight velocity, enabling the orthogonal MALDI to measure the heavy masses of intact proteins much more accurately than conventional in-line MALDI or electro-spray mass spectrometers.

The inventive process detailed herein is well suited for performing kinetic or sample constituent ratio studies for a sample containing known proteinaceous and/or viral constituents. The metabolic or physiological status of a cell culture or organism is regularly defined by the ratio of various proteinaceous substances. Similarly, variations between viral populations within a host organism or culture afford important information with regard to sample origin. Through the washing and elution denoted at steps 3 and 4 with respect to FIG. 1 with separation buffers preselected with respect to protein or viral constituents of a sample and otherwise continuing an inventive process as described herein with respect to FIG. 1, 10 or 11 is operative to yield the metabolic status and/or the identity of a sample origin. The parallel automation of the present invention affords efficiencies that make such previously time-consuming studies practical.

By way of example, bacterial spore age, metabolic state, and strain information illustratively are derived from a spore lysate sample subjected to parallel separation according to the present invention with separation buffers selected for the purification of known spore constituents. This aspect of the present invention is particularly useful in salmonella, clostridium and anthracis outbreaks in forensic and public health investigations.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for analyzing proteins or viruses in a sample comprising:
    dividing a sample having a protein or virus component into a plurality of n aliquots;
    simultaneously applying each of said plurality of n aliquots in parallel and separately to a first separation step comprising:
    washing each of said n aliquots with a corresponding buffer $C_{n-1}$ of a monotonically changing buffer set $C_{n-1}$ to $C_n$ to yield a plurality of first n fractions;
    eluting each of said washed n aliquots with a corresponding buffer $C_n$ to yield a plurality of uniquely different partially resolved first n eluates;
    simultaneously subjecting said plurality of partially resolved first n eluates in parallel to a second separation step to yield a plurality of second n resolved fractions, and
    analyzing at least one of said plurality of second n resolved fractions.

2. The process of claim 1 further comprising collecting at least one of said plurality of resolved fractions.

3. The process of claim 2 wherein collection of the at least one of said plurality of resolved fractions occurs onto a MALDI target or plate.

4. The process of claim 3 further comprising the step of analyzing at least one of said plurality of resolved fractions by mass spectrometry wherein said mass spectrometry is performed on an orthogonal MALDI mass spectrometer.

5. The process of claim 1 wherein analysis is by mass spectrometry.

6. The process of claim 5 wherein said mass spectrometry is performed on a MALDI mass spectrometer.

7. The process of claim 1 wherein at least one of said first and said second separation steps separate on a basis selected from the group consisting of: charge, molecular weight, and hydrophobicity.

8. The process of claim 1 wherein at least one of said first and said second separation steps uses a chromatography resin or chromatography membrane.

9. The process of claim 1 wherein at least one of said first and said second separation steps comprises a separation buffer that varies monotonically between individual aliquots or individual eluates.

10. The process of claim 1 wherein at least one of said first and said second separation steps comprises a separation matrix in linear or two-dimensional array.

11. The process of claim 10 wherein said first and said second separation steps occur with matrices maintaining well addresses in each of the two matrices.

12. The process of claim 1 wherein at least one of said first or said second separation steps occurs within a microplate.

13. The process of claim 1 further comprising: digesting said plurality of partially resolved eluates prior to subjecting said plurality of partially resolved eluates in parallel to said second separation step.

14. The process of claim 1 wherein the step of applying said plurality of aliquots in parallel to said first separation step is performed by a robot.

15. The process of claim 1 further comprising affixing a machine-readable label to at least one collection selected from the group consisting of: said plurality of aliquots, said plurality of partially resolved eluates, and said plurality of resolved fractions.

16. The process of claim 1 further comprising the steps of:
labeling a subsample with a unique tag; and
combining said subsample with a second uniquely labeled subsample or an unlabeled subsample prior to said plurality of aliquots.

17. A process for analyzing proteins or viruses in a sample comprising:
dividing a sample having a protein or virus component into a plurality of n aliquots;
simultaneously applying each of said plurality of n aliquots in parallel and separately to a first separation step comprising:
washing each of said n aliquots with a corresponding buffer $C_{n-1}$ of a monotonically changing buffer set $C_{n-1}$ to $C_n$ to yield a plurality of first n fractions;
eluting each of said washed n aliquots with a corresponding buffer $C_n$ to yield a plurality of uniquely different partially resolved first n eluates;
digesting said plurality of partially resolved first n eluates with a proteolytic enzyme to yield a plurality of digested eluates;
subjecting said plurality of digested eluates in parallel to a second separation step to yield a plurality of second n resolved fractions, and
analyzing at least one of said plurality of second n resolved fractions.

18. The process of claim 17 further comprising: collecting at least one of said plurality of resolved fractions.

19. The process of claim 18 wherein collection of the at least one of said plurality of resolved fractions occurs onto a MALDI target or plate.

20. The process of claim 17 wherein analysis is by mass spectrometry.

21. The process of claim 20 wherein said mass spectrometry is performed on an orthogonal MALDI mass spectrometer.

22. The process of claim 17 wherein at least one of said first and said second separation steps separate on a basis selected from the group consisting of: charge, molecular weight, and hydrophobicity.

23. The process of claim 17 wherein at least one of said first and said second separation steps comprises a separation buffer that varies monotonically between individual aliquots or individual eluates.

24. The process of claim 17 wherein at least one of said first and said second separation steps comprises a separation matrix in linear or two-dimensional array.

25. The process of claim 24 wherein said first and said second separation steps occur with matrices maintaining well addresses in each of the two matrices.

26. The process of claim 17 wherein at least one of said first or said second separation steps occurs within a microplate.

27. The process of claim 17 further comprising analyzing at least one of said plurality of partially resolved eluates prior to digestion in concert with the corresponding resolved fraction.

28. The process of claim 27 wherein analysis is by mass spectrometry.

* * * * *